US00PP15385P2

(12) United States Plant Patent
Olesen et al.

(10) Patent No.: US PP15,385 P2
(45) Date of Patent: Nov. 30, 2004

(54) ROSE PLANT NAMED 'POULPM003'

(50) Latin Name: *Rosa hybrid*
Varietal Denomination: POULpm003

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/812,740

(22) Filed: Mar. 29, 2004

(51) Int. Cl.[7] ..... A01H 5/00
(52) U.S. Cl. ..... Plt./134
(58) Field of Search ..... Plt./134

*Primary Examiner*—Anne Marie Grunberg
*Assistant Examiner*—Annette H Para

(57) ABSTRACT

A new garden rose plant of the hybrid tea class which has abundant, yellow flowers and attractive foliage. This new and distinct variety has shown to be uniform and stable in the resulting generations from asexual propagation.

2 Drawing Sheets

Botanical classification: *Rosa hybrid*.
Variety denomination: 'POULpm003'.

SUMMARY OF THE INVENTION

The present invention constitutes a new and distinct variety of garden rose plant which originated from a controlled crossing between the female seed parent, an un-named seedling, and the male pollen parent, 'FRYjingo', a non-patented rose variety. The two parents were crossed during the summer of 1993 and the resulting seeds were planted in a controlled environment in Fredensborg, Denmark. The new variety is named 'POULpm003'.

The new variety may be distinguished from its female seed parent, an un-named seedling, by the following combination of characteristics:

1. While the seed parent has an open flower size of 100–130 mm, 'POULpm003' is 80 mm.
2. The seed parent has a higher average petal count than 'POULpm003'.

The new variety may be distinguished from its male pollen parent, 'FRYjingo' by the following combination of characteristics:

1. While the pollen parent has more orange and red pigment in the flower color than 'POULpm003'.
2. The pollen parent has more of an uneven growth habit than 'POULpm003'.

The objective of the hybridization of this rose variety was to create a new and distinct variety for garden use with unique qualities, such as:

1. Uniform and abundant yellow flowers;
2. Vigorous, compact, and even growth when propagated as a budded rose and on its own roots;
3. Disease resistance.

This combination of qualities is not present in previously available commercial cultivars of this type, known to the inventors, and distinguish 'Poulpm003' from all other varieties of which we are aware.

As part of their rose development program, L. Pernille Olesen and Mogens N. Olesen germinated the seeds from the aforementioned hybridization during winter of 1994 and conducted evaluations on the resulting seedlings in a controlled environment in Fredensborg, Denmark.

'POULpm003' was selected in the spring of 1994 by the inventors as a single plant from the progeny of the aforementioned hybridization.

Asexual reproduction of 'POULpm003' by traditional budding and rooted cuttings was first done by L. Pernille and Mogens N. Olesen in their nursery in Fredensborg, Denmark in July, 1994. This initial and other subsequent asexual propagations conducted in controlled environments have demonstrated that the characteristics of 'POULpm003' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULpm003'.

Specifically illustrated in FIG. 1:

FIG. 1.1; Open flower from above, and open flower from the side showing attachment of sepals and peduncle;

FIG. 1.2; Flower bud closed, flower bud as sepals unfold, and partially open;

FIG. 1.3; Sepals, receptacle, and peduncle;

Specifically illustrated in FIG. 2:

FIG. 2.1; Petals, detached;

FIG. 2.2; Juvenile shoot, leaves, and flower bud exhibiting anthocyanin;

FIG. 2.3; Mature trifoliate leaf;

FIG. 2.4; Bare stems.

DETAILED DESCRIPTION OF THE VARIETY

The following is a description of 'POULpm003', as observed in its growth in in a field nursery in Jackson County, Oreg. Observed plants are 3 years of age, and were grown on *Rosa multiflora* understock. Color references are made using The Royal Horticultural Society (London, England) Colour Chart, 1995, except where common terms of color are used.

For a comparison, several physical characteristics of the rose variety 'Wingold', described and illustrated in U.S. Plant Pat. No. 12,739 dated Jul. 2, 2002 are compared to 'POULpm003' in Chart 1.

CHART 1

| | 'Poulpm003' | 'Wingold' |
|---|---|---|
| General tona1ity. | Yellow Group 4D. | Yellow Group 11D. |
| Petalage. | 30 petals | 23. |
| Petal Color upon opening: inner petals upper surface | Yellow Group 6C with light intonations of Yellow-Orange Group 22A at petal margins | Yellow Group 11C |

FLOWER AND FLOWER BUD

Blooming habit: Recurrent.

Flower bud:

*Size.*—Upon opening, 30 mm in length from base of receptacle to end of bud. Bud diameter is 20 mm.

*Bud form.*—Broad based.

*Bud color.*—As sepals unfold, petals are Yellow-Green Group 150C with intonations of Red Group 47B at petal margins. At ¼ opening petals change color to Yellow Group 6C.

*Sepals.*—Upper Surface: Color: Yellow-Green Group 145A. Surface: Somewhat pubescent. Lower Surface: Color: Yellow-Green Group 144A–B. Anthocyanic pigments the color of Greyed-Red Group 179A observed. Texture: Smooth. Stipitate glands observed, medium in quantity. Sepal Shape: Sepal apex is cirrhose. Base is flat at union with receptacle. Sepal Margin: Margins have medium foliaceous appendages on three of the five sepals. Size: 35 mm long by 12 mm wide.

*Receptacle.*—Surface Texture: Smooth. Shape: Broadly funnel shaped. Size: 5 mm (h)×12 mm (w). Color: Yellow-Green Group 144A.

*Peduncle.*—Surface: Smooth with few stipitate glands. Length: 60 to 70 mm average length. Color: Yellow-Green Group 144A. Strength: Strong.

*Borne.*—Singularly.

Flower bloom:

*Fragrance.*—Moderate rose.

*Duration.*—The blooms have a duration on the plant of approximately 10 to 14 days. Petals fall cleanly away from plant after flowers have fully matured.

*Size.*—Flower diameter is 80 mm when open. Average flower depth is 40 mm.

*Form.*—General shape is a deep cup, double flower, with petals that curve out from the center.

*Form.*—Viewed from the side: Upon opening, upper part: Flat. Upon opening, lower part: Concave. Open flower, upper part: Flat. Open flower, lower part: Concave.

*Petalage.*—30 petals under normal conditions with 3 petaloids.

Color:

*Upon opening, petals.*—Outermost petals: Outer side: Yellow Group 4D. Inner Side: Yellow Group 4D. Innermost petals: Outer side: Yellow Group 6C with light intonations of Yellow-Orange Group 22A at petal margins. Inner Side: Yellow Group 6C with light intonations of Yellow-Orange Group 22A at petal margins.

*Upon opening, basal petal spots.*—No distinctive coloration at the petal base observed.

*After opening, petals.*—Outermost petals: Outer side: Yellow Group 4D. Inner Side: Yellow Group 4D. Innermost petals: Outer side: Yellow Group 4D. Inner Side: Yellow Group 4D.

*After opening, basal petal spots.*—No distinctive coloration at the petal base observed.

General tonality: On open flower Yellow Group 4D. No change in the general tonality at the end of the $10^{th}$ day.

Petals:

*Petal reflex.*—Somewhat reflexed.

*Margin.*—Entire and uniform.

*Shape.*—Apex is rounded. Base is rounded, somewhat acute.

*Size.*—58 mm (l)×58 mm (w).

*Texture.*—Smooth.

*Thickness.*—Thick.

*Arrangement.*—Formal.

Petaloids:

*Quantity.*—1 to 4.

*Shape.*—Apex is rounded. Base is rounded, somewhat acute.

*Color.*—Upper and lower surfaces are Yellow Group 4D.

*Size.*—45 mm (l)×35 mm (w).

Reproductive organs:

*Pollen.*—None observed.

*Anthers.*—Size: 3 mm in length. Color: Greyed-Yellow Group 160A. Quantity: 230 (actual count).

*Filaments.*—Color: Yellow-Orange Group 14A to 17A. Length: 7 mm.

*Pistils.*—Length: 10 mm. Quantity: 140 (actual count).

*Stigmas.*—Superior in location relative to the length of the filaments and the height of the anthers. Color: Greyed-Yellow Group 160A.

*Styles.*—Color: Green-White Group 157A. Intonations of Red-Purple Group 61C observed.

*Hips.*—None Observed in the field nursery in Jackson County, Oreg.

PLANT

Plant growth: Upright to bushy. When grown as a budded field grown plant on *Rosa multiflora* understock, the average height of the plant is 60 to 100 cm. Average spread is 60 to 80 cm.

Stems:

*Color.*—Young wood: Yellow-Green Group 146C. Older wood: Yellow-Green Group 146C.

*Surface texture.*—Young wood: Smooth. Older wood: Smooth.

Thorns:

*Incidence.*—5 thorns per 10 cm of stem.

*Size.*—Average length: 8 mm.

*Color.*—Greyed-Yellow Group 160A.

*Shape.*—Highly convex.

Plant foliage: Normal number of leaflets on normal leaves in middle of the stem: 5 leaflets.

*Compound leaf size.*—150 mm (l)×90 mm (w).

*Color.*—Mature Foliage: Upper surface is: Yellow-Green Group 146A. Lower surface is: Yellow-Green Group 147C. Juvenile foliage: Upper surface is: Yellow-Green Group 144A. Lower surface is: Yellow-Green Group 144B. Anthocyanin: Location: Juvenile leaves. Color: Greyed-Red Group 178A.

Plant leaves and leaflets:

*Stipules.*—Size: 25 mm long. Shape: Linear, slightly broad based with outward extending apeces. Quantity: 2 per compound leaf. Margins: Finely serrated with medium stipitate glands. Color: Yellow-Green Group 144A.

*Petiole.*—Length: 35 mm. Above: Color: Yellow-Green Group 144C. Anthocyanin: Upper surface: Greyed-Red Group 181C. Lower surface: Numerous stipitate glands and thorns observed.

*Rachis.*—Length: 60 mm. Above: Color: Yellow-Green Group 144C. Anthocyanin: Upper surface: Greyed-Red Group 181C. Underneath: Observations: Numerous stipitate glands and thorns observed.

*Leaflet.*—Edge: Serrated. Size: 50 mm (l)×40 mm (w). Shape: Ovate. Bas is rounded. Apex is acute. Texture: Smooth. Thickness: Thick. Arrangement: Odd pinnate. Venation: Reticulate. Glossiness: Matte finish.

Disease resistance: Above average resistance to mildew, rust, black spot, and Botrytis under normal growing conditions in Jackson County, Oreg.

Cold hardiness: The variety 'POULpm003' has been found to be cold tolerant to USDA Cold Hardiness Zone 6.

We claim:

1. A new and distinct variety of rose plant of the hybrid tea rose class named 'POULpm003', described and illustrated as a distinct and novel rose variety due to its abundant yellow flowers, disease resistance, and extended period of bloom.

* * * * *

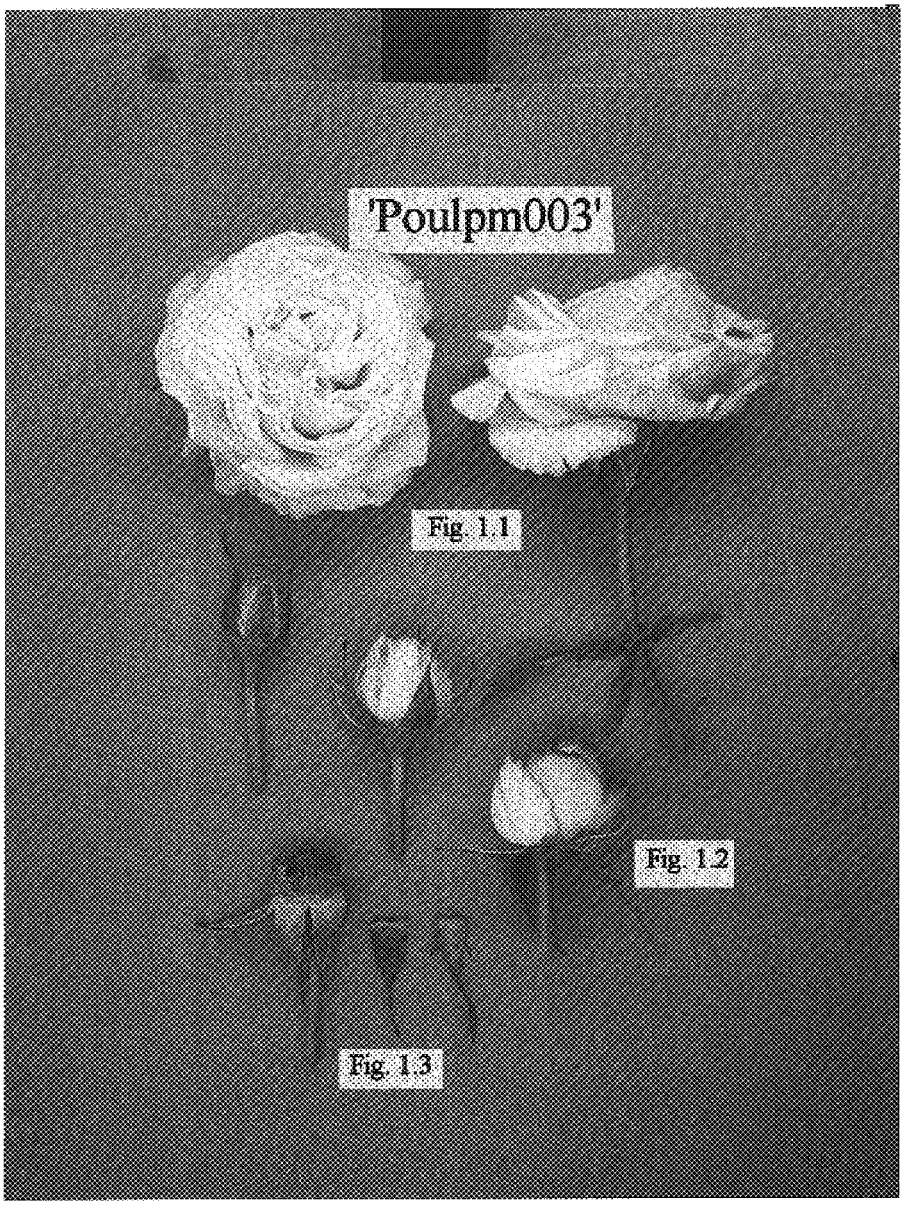
'Poulpm003'
Fig. 1.1
Fig. 1.2
Fig. 1.3

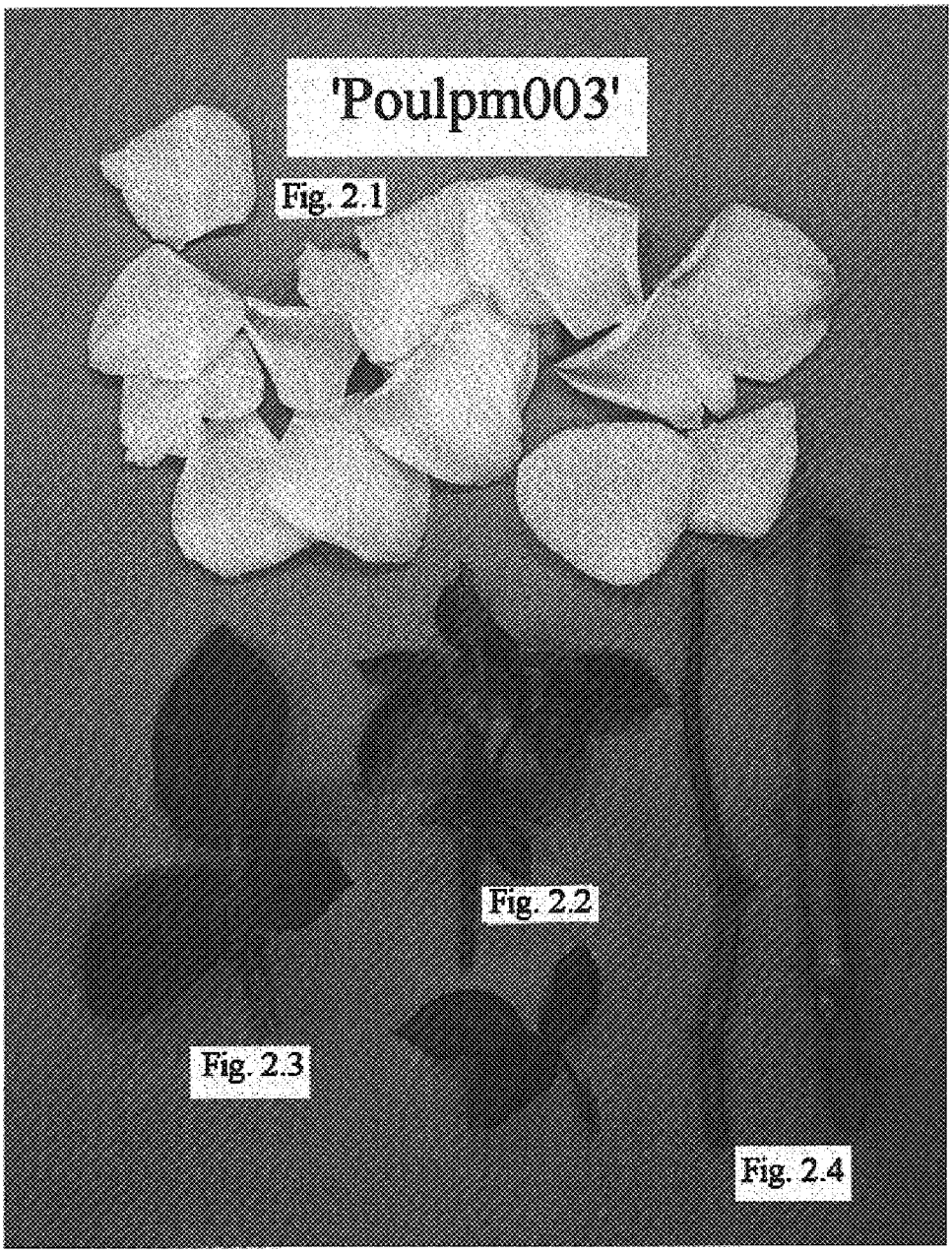
'Poulpm003'
Fig. 2.1
Fig. 2.2
Fig. 2.3
Fig. 2.4